United States Patent [19]
Cain et al.

[11] Patent Number: 5,317,024
[45] Date of Patent: May 31, 1994

[54] ETHER DERIVATIVES OF ALKYL PIPERIDINES AND PYRROLIDINES AS ANTIPSYCHOTIC AGENTS

[75] Inventors: Gary A. Cain, New Castle, Del.; Thomas E. Christos, Oxford, Pa.; Sang W. Tam, Hockessin, Del.

[73] Assignee: DuPont Merck Pharmaceutical Co., Wilmington, Del.

[21] Appl. No.: 98,443

[22] Filed: Aug. 3, 1993

Related U.S. Application Data

[62] Division of Ser. No. 589,863, Sep. 28, 1990, Pat. No. 5,252,586.

[51] Int. Cl.$^5$ .................. C07D 211/06; A01N 43/40
[52] U.S. Cl. ............................ 514/317; 514/319; 514/327; 514/331; 514/424; 514/428; 546/192; 546/205; 546/216; 546/221; 546/229; 546/232; 546/233; 546/234; 546/235; 546/236; 546/237; 546/239; 546/241; 548/544; 548/556
[58] Field of Search ............... 514/317, 319, 327, 331, 514/424, 428; 546/192, 205, 216, 221, 229, 232, 233, 234, 235, 236, 237, 239, 241; 548/544, 556

[56] References Cited

U.S. PATENT DOCUMENTS

| | | | |
|---|---|---|---|
| 4,104,383 | 8/1978 | Krausz | 546/192 |
| 4,866,062 | 9/1989 | Toth | 514/255 |
| 4,871,748 | 10/1989 | Hatton | 546/236 |
| 4,873,262 | 10/1989 | Junge | 514/255 |
| 5,169,855 | 12/1992 | Cain | 514/319 |

FOREIGN PATENT DOCUMENTS

| | | |
|---|---|---|
| 061710 | 8/1969 | Japan . |
| 065641 | 8/1971 | Japan . |
| 9109549 | 7/1991 | PCT Int'l Appl. . |

*Primary Examiner*—C. Warren Ivy
*Assistant Examiner*—Raymond Covington
*Attorney, Agent, or Firm*—Gerald J. Boudreaux

[57] ABSTRACT

Novel unsaturated ether derivatives of alkyl piperidine and pyrrolidine compounds, pharmaceutical compositions containing them, methods of preparation and methods of using these compounds as antipsychotic agents are disclosed.

13 Claims, No Drawings

ETHER DERIVATIVES OF ALKYL PIPERIDINES AND PYRROLIDINES AS ANTIPSYCHOTIC AGENTS

This is a division of application Ser. No. 07/589,863, filed Sep. 28, 1990, U.S. Pat. No. 5,252,586.

FIELD OF THE INVENTION

This invention relates to novel unsaturated ether derivatives of alkyl piperidine and pyrrolidine compounds, pharmaceutical compositions containing them, methods of preparation, and methods of using these compounds as antipsychotics.

BACKGROUND OF THE INVENTION

Traditional antipsychotic agents such as phenothiazines, e.g., chlorpromazine, and most butyrophenones, e.g., haloperidol, are potent dopamine receptor antagonists which produce a number of undesirable and irreversible side effects such as Parkinson-like motor effects or extra-pyramidal side-effects (EPS), and dyskinesias including tardive dyskinesias at high doses.

JA 065641, Abstract, Aug. 26, 1971 describes propenylamine derivatives useful as antipsychotic, analgesic, antihypertensive and antiinflammatory agents.

JA 061710, Abstract, Aug. 6, 1969, describes 4-amino-2-butynyloxy beta-nitro-styrenes useful as antitumor agents which can be prepared from 2-propionyl-beta-nitro-styrenes.

SUMMARY OF THE INVENTION

The compounds of the present invention have the formula:

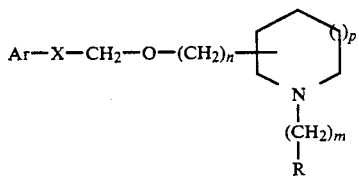

(I)

wherein:
n is 0, 1, or 2;
p is 0 or 1;
m is 1, 2, or 3;
X is —C=C— or $R^1C\equiv CR^2$ (cis or trans);
$R^1$ and $R^2$ independently are H, alkyl of 1–4 carbon atoms, or phenyl;
Ar is naphthyl or phenyl, optionally substituted with 1–5 substituents individually selected from $NO_2$, halogen, $CF_3$, SH, alkyl of 1–4 carbon atoms, alkoxy of 1–4 carbon atoms, hydroxy alkyl of 1–4 carbon atoms,

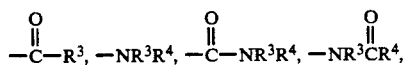

or $S(O)_q R^5$ where q is 0, 1, or 2;
$R^3$ and $R^4$ independently are H, alkyl of 1–4 carbon atoms, or phenyl;
$R^5$ is alkyl of 1–4 carbon atoms or phenyl;
R is H, alkyl of 1–5 carbon atoms, cycloalkyl of 3–6 carbon atoms, Arl where Arl is phenyl or naphthyl, or —CH=$CR^6R^7$; and
$R^6$ and $R^7$ independently are H or alkyl of 1–4 carbon atoms, provided that when n=0 the side chain is not located at the 2-position of the ring; or a pharmaceutically acceptable salt thereof.

This invention also includes pharmaceutical compositions containing these compounds.

In another embodiment, this invention includes a method of using these compounds as antipsychotic agents.

Finally, this invention includes processes for making the compounds of this invention.

DETAILED DESCRIPTION OF THE INVENTION

Compounds of the invention are related to antipsychotic agents which are selective sigma receptor antagonists rather than the traditional dopamine receptor blockers known in the art. Accordingly, the compounds of this invention antagonize aggressive behavior and hallucinogenic-induced behavior without exhibiting any substantial movement disorder side-effects typically associated with dopamine antagonist antipsychotic agents.

Compounds of the invention have the formula:

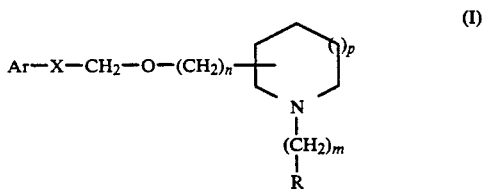

(I)

wherein:
n is 0, 1, or 2;
p is 0 or 1;
m is 1, 2, or 3;
X is —C=C— or $R^1C\equiv CR^2$ (cis or trans);
$R^1$ and $R^2$ independently are H, alkyl of 1–4 carbon atoms, or phenyl;
Ar is naphthyl or phenyl, optionally substituted with 1–5 substituents individually selected from $NO_2$, halogen, $CF_3$, SH, alkyl of 1–4 carbon atoms, alkoxy of 1–4 carbon atoms, hydroxy alkyl of 1–4 carbon atoms,

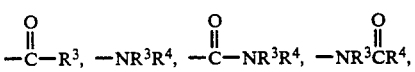

or $S(O)_q R^5$ where q is 0, 1, or 2;
$R^3$ and $R^4$ independently are H, alkyl of 1–4 carbon atoms, or phenyl;
$R^5$ is alkyl of 1–4 carbon atoms or phenyl;
R is H, alkyl of 1–5 carbon atoms, cycloalkyl of 3–6 carbon atoms, $Ar^1$ where $Ar^1$ is phenyl or naphthyl, or —CH=$CR^6R^7$; and
$R^6$ and $R^7$ independently are H or alkyl of 1–4 carbon atoms, provided that when n=0 the side chain is not located at the 2-position of the ring; or a pharmaceutically acceptable salt thereof. Preferred compounds are those of formula (I) where:
1) n and p are 1; and/or
2) m is 1–3; and/or
3) R is phenyl; and/or
4) X is trans —CH=CH—; and/or
5) Ar is phenyl, p-F-phenyl, or p-$CF_3$-phenyl; and/or
6) the side chain is attached at the 4-position of the piperidine ring.

Specifically preferred compounds of the present invention include:
a) (E)-1-benzyl-4-[(3-phenyl-2-propenyloxy)methyl] piperidine, hydrochloride salt
b) (E)-1-benzyl-4-{[3-(4-fluoro)phenyl-2-propenyloxy]methyl} piperidine, hydrochloride salt
c) (E)-1-phenethyl-4-[(3-phenyl-2-propenyloxy)methyl] piperidine, hydrochloride salt
d) (E)-1-(3-phenyl)propyl-4-[(3-phenyl-2-propenyloxy)methyl]piperidine, hydrochloride salt
e) (E)-1-benzyl-4-{[3-(4-trifluoromethyl)phenyl-2-propenyloxy]methyl}piperidine, maleic acid salt.

Compounds of formula (I), provided that X is not C≡C, can be prepared according to Scheme I, wherein a compound of formula (II) is treated with base in an inert solvent, then allowed to react with a compound of formula (III).

Suitable bases which can be used include, alkali metal hydrides, preferably sodium hydride, alkali metal dialkylamides, preferably lithium diisopropylamide, alkali metal bis(trialkylsilyl)amides, preferably sodium bis(trimethylsilyl)amide, alkyl alkali metal compounds, such as n-butyl lithium, or alkyl alkaline earth metal halides, such as methyl magnesium bromide. As those skilled in the art will appreciate, the inert solvent selected should be compatible with the base selected. carbon atoms, cyclic ethers of 4 to 10 carbon atoms, preferably tetrahydrofuran, dialkylformamides, preferably N,N-dimethylformamide, cyclic amides, such as N-methylpyrrolidinone, or cyclic dialkylureas, such as N,N$^1$-dimethylpropyleneurea.

Compounds of formula (III) possess a leaving group designated "Y" which can be a halide, arylsulfonyloxy, preferably p-toluenesulfonyloxy, alkylsulfonyloxy, such as methanesulfonyloxy, or haloalkylsulfonyloxy, such as trifluoromethylsulfonyloxy.

Reaction temperatures range from about −78° C. to 100° C., preferably about 0° C. to 25° C.

Compounds of formula (I) can alternatively be prepared according to Scheme II. According to Scheme II, a compound of formula (IV) bearing a deactivated ring nitrogen is treated first with base in an inert solvent and then is reacted with a compound of formula (III) to provide a compound of formula (V). The choice of base, solvent, reaction temperature, and leaving group Y is based upon the same parameters as described above for Scheme I.

The substituent Z can be $(CH_2)m-1^R$ as defined above, or Z can be alkoxy or aryloxy except that when m=2, R may not be $Ar^1$.

Compounds of formula (V) are converted into compounds of formula (I) depending on the choice of Z. When Z is $(CH_2)m-1^R$, these compounds can be treated with reducing agents in inert solvents to yield products of formula (I).

Suitable reducing agents include alkali metal aluminum hydrides, preferably lithium aluminum hydride, or alkali metal alkoxy-aluminum hydrides, such as lithium tri-t-butoxyaluminum hydride. Inert solvents include, but are not limited to, ethereal solvents such as diethyl ether or tetrahydrofuran. Reduction temperatures range from about −78° C. to about 25° C.

When Z is alkoxy or aryloxy [a wide range of these carbamates can be used, as is taught in T. W. Greene, *Protective Groups in Organic Synthesis* (J. Wiley & Sons, New York, 1981) pp. 223–266] the carbamate can be cleaved under standard conditions as described in the Greene reference to yield a compound of formula (VI). The amines of formula (VI) can then be alkylated by treatment with a compound of formula (VII) in the presence of a base in an inert solvent to yield the desired compounds of formula (I).

The choice of base includes those described above for Scheme I as well as alkali metal carbonates, preferably potassium carbonate, trialkylamines, such as triethylamine or diisopropylethylamine, or polycyclic diamines, such as 1,4-diazabicyclo-[2.2.2]-octane or 1,8-diazabicyclo-[5.4.0]-undecene. Appropriate solvents include those described above for Scheme I as well as lower alkyl alcohols of 1 to 6 carbons, or halocarbons, such as chloroform or dichloromethane.

Suitable reaction temperatures range from about −78° C. to about 100° C., preferably −78° C. to 25° C. The type of leaving group Y includes those described above for Scheme I. The choice of Y, base, solvent, and reaction temperature will be readily apparent to those skilled in the art.

Scheme I

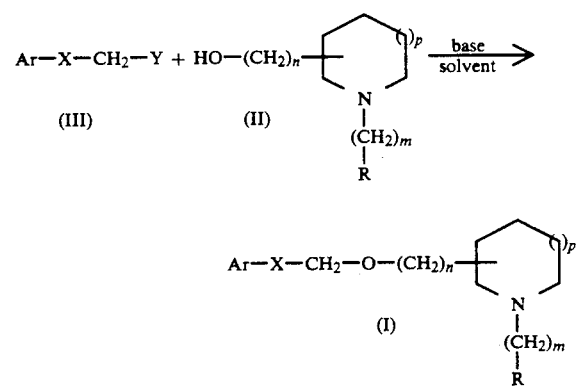

Scheme II

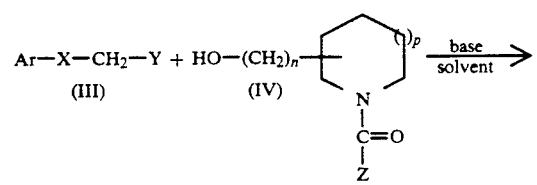

Scheme II

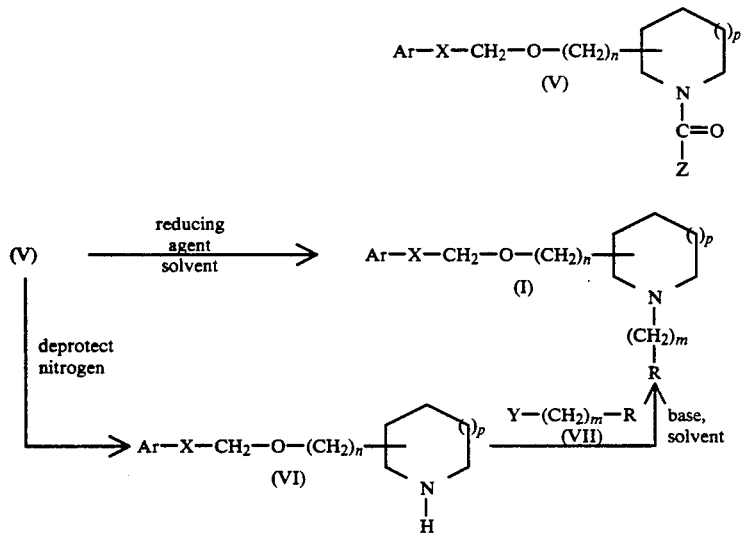

The intermediate of formula (V) can alternately be prepared according to Scheme III by treating an alcohol of formula (VIII) with base in an inert solvent, then allowing the resulting product to react with a compound of formula (IX) to provide the desired ether. Choices of leaving group Y, substituent Z, base, and inert solvent include those described above for Scheme I. Preferably, Y is methane sulfonyloxy or p-toluenesulfonyloxy, Z is phenyl or O-t-butyl, the base is sodium hydride, the solvent is N,N¹-dimethylformamide, and the reaction temperature is from 0° C. to reflux.

Scheme III

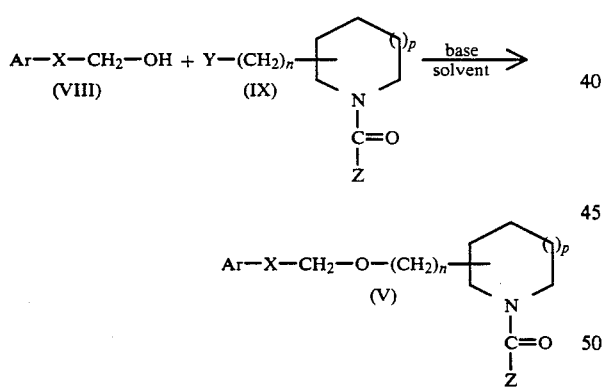

A particularly expeditious route to the compounds of formula (I), when X is cis CH=CH (Ib), shown in Scheme IV, is via partial reduction of the acetylenic intermediates of formula (Va) to provide the cis allylic ethers- of formula (Vb), followed by conversion of the

group to N-(CH$_2$)$_m$R as described earlier.

A wide variety of metros and conditions are known in the literature for performing the partial reduction of acetylenes to cis olefins (see J. March, *Advanced Organic chemistry*, 3rd Ed., J. Wiley & Sons, New York, 1985, Chapter 15 and references cited therein). The most preferred method for this partial reduction is via treatment of (Va) with a catalytic amount of 5% palladium on barium sulfate and synthetic quinoline in methanol under 1 atmosphere of hydrogen at ambient temperature, carefully monitoring the amount at H$_2$ uptake while following the reaction progress by TLC.

Scheme IV

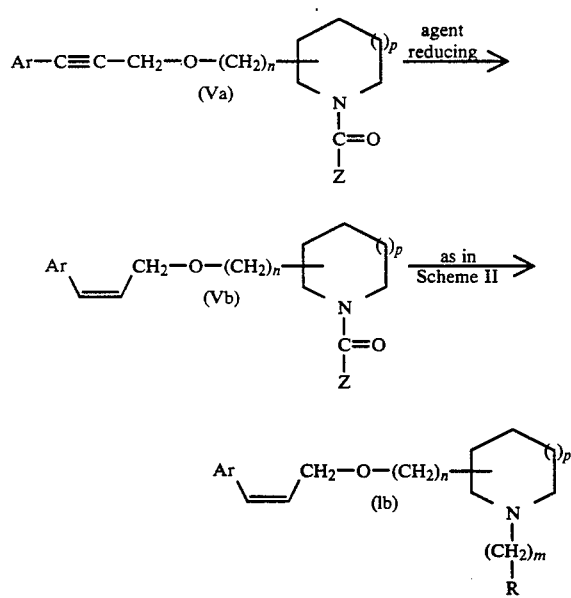

The alkylamino alcohol intermediates of formula (II) can be prepared via one of the two routes shown in Scheme V. In one route, a hydroxyamine of formula (X), which is either available commercially or can be synthesized using standard techniques as described in the chemical literature, is treated with an alkylating agent of formula (VII) in the presence of a base in an inert solvent as was described above for the alkylation of amine (VI) to produce the intermediate (II).

Alternately, an ester of formula (XI), except for n=0, can be alkylated with (VII) under the same conditions to produce an ester of formula (XII), which is then further reduced to the alcohol intermediate (II) by treatment with a reducing agent in an inert solvent.

The choice of reducing agent includes alkali metal aluminum hydrides, preferably lithium aluminum hydride, alkali metal alkoxyaluminum hydrides, such as lithium tri-t-butoxyaluminum hydride, alkali metal borohydrides, preferably lithium borohydride, dialkylaluminum hydrides, such as diisobutylaluminum hydrides, alkali metal trialkylboron hydrides, such as lithium tri-s-butylboron hydride Appropriate solvents include ethers such as diethyl ether or tetrahydrofuran. Reaction temperatures range from about −78° C. to about 100° C., preferably from about 0° C. to about 25° C.

Chem. (1982), 47, 1604; (1984), 49, 3891) to yield the desired product (IV).

Scheme VI

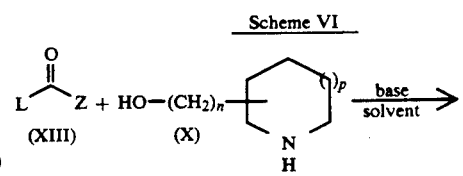

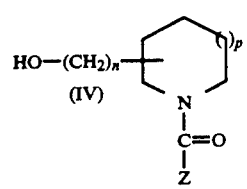

Scheme V

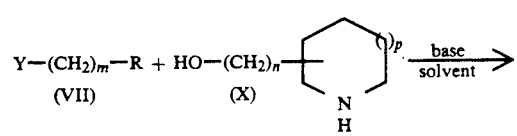

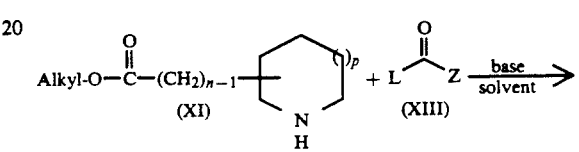

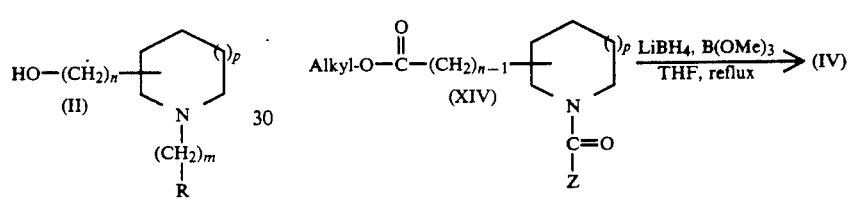

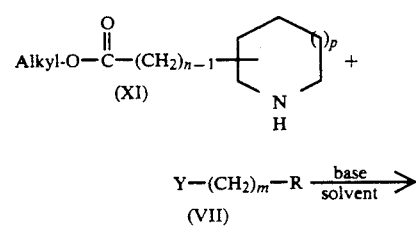

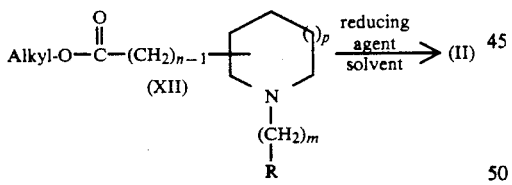

The protected amino alcohol intermediates of formula (IV) can be prepared by one of the routes shown in Scheme VI. An amino alcohol of formula (X) is treated with an acylating agent of formula (XIII) in the presence of a base in an inert solvent to produce the protected amine of formula (IV).

The conditions for acylation of amines to form amides and carbamates are quite varied; the above cited Green reference (Chapter 7) provides a multitude of procedures and examples.

Alternately, an amino ester of formula (XI), except for n=0, can be N-acylated with an agent (XIII) as described above to provide a protected amino ester of formula (XIV). The ester group of compound (XIV) is then selectively reduced to an alcohol in the presence the acyl amine using the lithium borohydride/methyl borate conditions reported by H. C. Brown (J. Org.

The intermediate compounds of formula (IX) described in Scheme III can be prepared from the N-protected alcohols of formula (IV) just described as illustrated in Scheme VII. A wide variety of methods are known for the conversion of alcohols into the leaving groups Y described earlier; see the above cited March reference (pp. 357–358, 381–384) and references cited therein.

Scheme VII

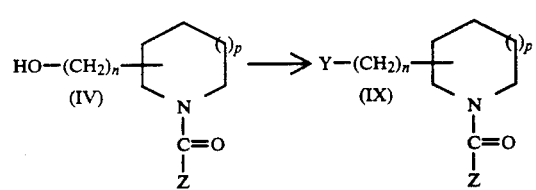

The unsaturated alcohol reagents of formula (VIII) are well known in the literature, being prepared by a variety of methods; see L. Brandsma, Preparative Acetylenic Chemistry, 2nd Ed., Elsevier, New York (1988), pp. 214–219; K. Sonogashira et al., Tet. Lett. (1975), 4467; G. Trivedi et al., Org. Prep. Proc. Int. (1985), 17, 251 and references cited therein for leading references.

As shown in Scheme VIII, the alcohol intermediates of formula (VIII) can be converted into the alkylating reagents of formula (III), with leaving groups Y as described earlier, via a number of standard methods as reported in the March reference cited above (pp. 357–358, 381–384)

Scheme VIII

Ar—X—(CH$_2$)OH ——> Ar—X—CH$_2$—Y
(VIII)                              (III)

The examples discussed below illustrate the synthesis of specific compounds of Formula (I) which constitute inter alia the subject matter of this invention.

Examples 1–16 describe the preparation of reagents of formula (II). Protected amino alcohol reagents of formula (IV) are prepared as described in Examples 17-8. Intermediates of formula (IX) are synthesized as described in Examples 19–20. Compounds of formula (I) can be prepared as described in Examples 21–42.

EXAMPLE 1

1-Benzyl-4-carboethoxypiperidine

Ethyl isonipecotate (212 g, 1 35 mole), benzyl chloride (170 g, 1.35 mole), and potassium carbonate (322 g, 233 mole) were stirred at room temperature in absolute EtOH (1.8 L) for 72 hours. The crude mixture was filtered through Celite, rinsed with Et$_2$O, and concentrated in vacuo. The resulting mixture was diluted with Et$_2$O, and extracted with H$_2$O (3×), then brine, dried (MgSO$_4$), and concentrated in vacuo. The product was distilled under high vacuum, bp 128°–130° C. at 0.8 mm Hg, to yield 252 g of a colorless liquid (76%). Analysis: Calculated for C$_{15}$H$_{21}$NO$_2$: C,72.84; H,8.56; N,5.66; found: C,72.91; H,8.38; N,5.88

Table 1 sets forth additional examples which can be prepared according to the procedure described in Example 1 above.

TABLE 1

[Structure: EtO-C(=O)-piperidine-N-R]

| Ex. No. | R | bp; (Torr) |
|---|---|---|
| 2 | cyclopropyl | 102–108° C. (0.8) |
| 3 | CH$_2$Ph | 140–145° C. (1.0) |
| 4 | 2-naphthyl | 186–188° C. (1.0) |
| 5 | CH=CMe$_2$ | 90–94° C. (0.7) |
| 6 | CH$_2$CH$_2$Ph | 160–164° C. (1.6) |
| 7 | 1-naphthyl | 175–183° C. (0.9) |

| | Analyses | | | | | |
|---|---|---|---|---|---|---|
| | Calculated | | | Found | | |
| Ex. No. | % C | % H | % N | % C | % H | % N |
| 2 | 68.21 | 10.02 | 6.63 | 68.27 | 9.90 | 6.78 |
| 3 | 73.53 | 8.87 | 5.36 | 73.61 | 8.92 | 5.55 |
| 4 | a) | | | | | |
| 5 | 69.29 | 10.29 | 6.22 | 69.32 | 10.32 | 6.29 |
| 6 | b) | | | | | |
| 7 | 76.74 | 7.80 | 4.71 | 76.68 | 7.83 | 4.68 | a) HRMS: calculated for C$_{19}$H$_{23}$NO$_2$: 297.1728; found: 297.1730.
b) HRMS: calculated for C$_{17}$H$_{25}$NO$_2$: 275.1885; found: 275.1884.

EXAMPLE 8

1Benzyl-4-hydroxymethylpiperidine

A solution of 1-benzyl-4-carboethoxypiperidine (74.3 g, 0.300 mole) in anhydrous Et$_2$O (740 mL) was stirred at 0° C. under N$_2$. Lithium aluminum hydride (11.4 g, 0.300 mole) was added in small portions over 0.5 hours. After an additional 2.5 hours, the reaction was carefully quenched with H20 (740 mL). The mixture was filtered through a Celite pad and rinsed with ethyl acetate (EtOAc), then the layers were separated. The aqueous layer was saturated with NaCl, then extracted with EtOAc (3×100 mL). The combined organics were extracted with brine, dried (MgSO4), and concentrated in vacuo. The resulting crude product was vacuum distilled, bp ~144° C. at 0.1 mm Hg, to yield the alcohol (55.8 g, 91%) as a colorless, viscous oil. Analysis Calculated for C$_{13}$H$_{19}$NO: C.,76.06; H,9.33; N,6.82; found: C.,75.87; H,9.16; N,6.55.

Table 2 sets forth additional examples which can be prepared according to the procedure described in Example 8 above.

TABLE 2

[Structure: HO-CH$_2$-piperidine-N-R]

| Ex. No. | R | mp or bp; (Torr) |
|---|---|---|
| 9 | cyclopropyl | 108–129° C. (1.2) |
| 10 | CH$_2$Ph | 88–91° C. |
| 11 | 2-naphthyl | 80–82° C. |
| 12 | CH=CMe$_2$ | 110–112° C. (1.2) |
| 13 | CH$_2$CH$_2$Ph | 57–58.5° C. |
| 14 | 1-naphthyl | 53–54° C. |

| | Analyses | | | | | |
|---|---|---|---|---|---|---|
| | Calculated | | | Found | | |
| Ex. No. | % C | % H | % N | % C | % H | % N |
| 9 | a) | | | | | |
| 10 | 76.67 | 9.65 | 6.39 | 76.43 | 9.51 | 6.24 |
| 11 | 79.96 | 8.29 | 5.49 | 79.80 | 8.17 | 5.79 |
| 12 | b) | | | | | |
| 13 | c) | | | | | |
| 14 | d) | | | | | | a) HRMS: calc'd for C$_{10}$H$_{19}$NO: 169.1467; found: 169.1467.
b) HRMS: calc'd for C$_{11}$H$_{21}$NO: 183.1623; found: 183.1625.
c) HRMS: calc'd for C$_{15}$H$_{23}$NO: 233.1780; found: 233.1777.
d) HRMS: calc'd for C$_{17}$H$_{21}$NO: 255.1623; found: 255.1619.

EXAMPLE 15

1-n-Hexyl-4-hydroxymethylpiperidine

4-Piperidine methanol (2.8 g, 24 mmol), n-hexyl iodide (3.5 mL, 24 mmol), and dry triethylamine (3.6 mL, 26 mmol) were stirred at room temperature under a nitrogen atmosphere for 21 hours. The mixture was diluted with ethyl acetate (500 mL) and extracted successively with 1.0 M aqueous NaOH (50 mL), H$_2$O (5 ×50 mL), and brine (50 mL). The organic phase was dried (MgSO$_4$), filtered, and concentrated in vacuo to yield a tan oil (4.1 g, 86%). MS:200 (MH+, base peak), 182 (NH+—H$_2$O, 35%). $^1$H NMR (300 MHz, CDCl$_3$/TMS/δ): 3.49(d,2H,J=6Hz), 2.98–2.89(m,2H), 2.33–2.28(m,2H), 1.95–1.22(m,17H), 0.90–0.86(m,3H).

EXAMPLE 16

1-Benzyl-3-hydroxymethylpiperidine

Prepared according to the same procedure as described above for Example 8 except that the starting material was 3-hydroxymethylpiperidine. IR (neat): 3344 cm$^{-1}$. HRMS: Calculated for C$_{13}$H$_{19}$NO: 205.1466; found: 205.1466.

EXAMPLE 17

1-Benzoyl-4hydroxyethylpiperidine

Benzoyl chloride (13.3 mL, 0.115 mole) was added dropwise over 0.5 hour to a 0° C. solution of 4-piperidineethanol (14.8 g, 0.115 mole) and dry triethylamine (18 mL, 0.13 mole) in dichloromethane with mechanical stirring. After 16 hours at room temperature, the mixture was quenched with 1.0 M aqueous NaOH (150 mL), then extracted with ethyl acetate (1 L). The organic phase was extracted further with H$_2$O (125 mL), then brine (125 mL), dried (MgSO$_4$), filtered, and concentrated in vacuo. The crude product was purified by chromatography on silica gel, eluting with chloroform to 6% methanol in chloroform, followed by concentration in vacuo and drying at 100° C. under high vacuum for 1.5 hour to yield a viscous oil (25.1 g, 94%). IR (neat): 3409 cm$^{-1}$ (s,br), 1613(s). HRMS: Calculated for C$_{14}$H$_{19}$NO$_2$: 233.1416; found: 233.1410.

EXAMPLE 18

1-t-Butyloxycarbonyl-4-hydroxyethylpiperidine

A solution of di-t-butyl dicarbonate (10 15 g, 47 mmol) in tetrahydrofuran (15 mL) was added slowly to a 0° C. solution of 4-hydroxyethylpiperidine (5.0 g, 39 mmol) and sodium hydroxide (1.86 g, 47 mmol) in THF. After stirring for 24 hours at room temperature, the mixture was poured into water (200 mL) and extracted with ethyl acetate (3×200 mL). The solution was dried (MgSO$_4$), filtered, and concentrated under vacuum to yield a colorless oil (9.0 g, quant.). $^1$H NMR (300 MHz, CDCl$_3$/TMS, δ): 4.1(m,2H), 3.7(q,2H,J=5 Hz), 2.7(br t,2H), 1.7(m,2H), 1.43(s,9H), 1.12-1.00(m,3H). MSCI: 230(MH+, base).

EXAMPLE 19

1-Benzoyl-4-(p-toluene sulfonyl)oxyethylpiperidine

A solution of p-toluene sulfonic anhydride (6.0 g, 18 mmol) in dichloromethane (50 mL) was added dropwise over 1 hour to a room temperature solution of 1-benzoyl-4-hydroxyethylpiperidine (4.3 g, 18 mmol) and dry triethylamine (2.8 mL, 2 mmol) in dichloromethane. After 2 hours, the mixture was diluted with ethyl acetate (500 mL) and extracted successively with H$_2$O (2 ×100 mL), cold 0.1 M aqueous HCl (100 mL), saturated aqueous NaHCO$_3$ (100 mL), and brine (50 mL), dried (MgSO$_4$), filtered, and concentrated in vacuo. The crude product was purified by chromatography on silica gel, eluting with ethyl acetate, and concentrated to yield a crystalline solid (6.2 g, 89%) which melted at 81°-83° C. Analysis: Calculated for C$_{21}$H$_{25}$NO$_4$S: C,65.09; H,6.50; N,3.61; S,8.27; found: C.,65.31; H,6.74; N,3.41; S,8.30.

EXAMPLE 20

1-t-Butyloxycarbonyl-4-methanesulfonyloxyethylpiperidine

Methanesulfonyl chloride (4.0 mL, 52 mmol) was added slowly to a 0° C. solution of 1-t-butyloxycarbonyl-4-hydroxyethylpiperidine (10.0 g, 43.7 mmol) and diisopropylethylamine (7.3 mL, 52 mmol) in dichloromethane (100 mL) with stirring under a nitrogen atmosphere. After 24 hours at room temperature, the mixture was extracted with water (4×100 mL), dried (MgSO$_4$), filtered, and concentrated in vacuo to yield a clear oil which crystallized upon standing. Mp:60°-63° C. MSCI:252(MH+, base). $^1$H NMR(300 MHz, CDCl$_3$/TMS, δ): 4.3(br t,2H), 4.1(br d,2H), 3.0(S,3H), 2.7(br t,2H), 1.7-1.1(m,16H).

EXAMPLE 21

(E)-1-Benzyl-4-[(3-phenyl-2-propenyloxy)methyl]-piperidine hydrochloride

Sodium hydride (0.80 g, 20 mmol, 60% oil disp.) and 1-benzyl-4-hydroxymethyl-piperidine (4.1 g, 20 mmol) were stirred at room temperature in dry tetrahydrofuran (40 mL) under a nitrogen atmosphere. After H$_2$ gas evolution had ceased (ca. 2 hours), cinnamyl chloride (2.8 mL, 20 mmol) was added. After 42 hours, the mixture was heated to reflux for 26.5 hours, then cooled. The reaction was quenched with water (40 mL), then extracted with ethyl acetate (200 mL). The organic phase was extracted with H$_2$O (40 mL), brine (40 mL), dried (MgSO$_4$), filtered, and concentrated in vacuo. The crude product was purified by chromatography on silica gel, eluting with ethyl acetate, concentrated, and distilled (bp 188°-190° C. at 0.6 Torr) to yield a pale yellow oil (2.72 g, 42%). HRMS: Calculated for C$_{22}$H$_{27}$NO: 321.2093; found: 321.2094.

To a solution of the free base (2.56 g, 8.0 mmol) in dry diethyl ether was added dropwise 1.0 M HCl in diethyl ether (8.8 mL, 8.8 mmol). A precipitate quickly formed, which was collected by filtration, rinsed with diethyl ether, and dried under high vacuum to yield the hydrochloride salt (2.5 g, 88%) which melted at 162°-164° C. Analysis: Calculated for C$_{22}$H$_{27}$NO·HCl: C,73,83; H,7.89; N,3.91; found: C.,73.35; H,7.91; N,4.00.

Table 3 sets forth additional examples which can be prepared according to the procedure described in Example 21 above.

TABLE 3

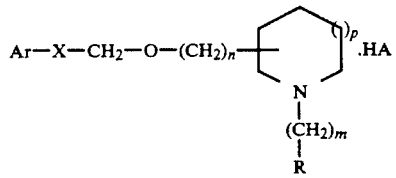

| Ex. No. | Ar | X | n | m | P | R | Isomer | A |
|---|---|---|---|---|---|---|---|---|
| 22 | 4-fluoro-Ph | trans CH=CH | 1 | 1 | 1 | Ph | 4 | Cl |
| 23 | Ph | trans CH=CH | 1 | 1 | 1 | cyclopropyl | 4 | Cl |
| 24 | Ph | trans CH=CH | 2 | 1 | 1 | Ph | 2 | Cl |
| 25 | Ph | trans CH=CH | 1 | 2 | 1 | Ph | 4 | Cl |
| 26 | Ph | trans CH=CH | 1 | 1 | 1 | 2-naphthyl | 4 | Cl |

TABLE 3-continued

| Ex. | | | | | | | | |
|---|---|---|---|---|---|---|---|---|
| 27 | Ph | trans CH=CH | 1 | 1 | 1 | Ph | 3 | Cl |
| 28 | Ph | trans CH=CH | 1 | 1 | 1 | Ph | 2 | Cl |
| 29 | Ph | trans CH=CH | 1 | 1 | 1 | CH=CMe$_2$ | 4 | maleate |
| 30 | Ph | trans CH=CH | 1 | 3 | 1 | Ph | 4 | Cl |
| 31 | Ph | trans CH=CH | 0 | 1 | 1 | Ph | 4 | maleate |
| 32 | Ph | trans CH=CH | 0 | 1 | 0 | Ph | 3 | maleate |
| 33 | Ph | trans CH=CH | 1 | 1 | 1 | 1-naphthyl | 4 | maleate |
| 34 | Ph | PhC=CH | 1 | 1 | 1 | Ph | 4 | Cl |
| 35 | 4-CF$_3$-Ph | trans CH=CH | 1 | 1 | 1 | Ph | 4 | maleate |
| 36 | Ph | trans CH=CH | 1 | 6 | 1 | H | 4 | maleate |
| 37 | Ph | trans CH=CH | 1 | 1 | 0 | Ph | 2-(R) | maleate |
| 38 | Ph | trans CH=CH | 1 | 1 | 0 | Ph | 2-(S) | maleate |

Analysis

| Ex. No. | mp °C. | Calculated | | | Found | | | Other |
|---|---|---|---|---|---|---|---|---|
| | | % C | % H | % N | % C | % H | % N | |
| 22 | | 70.29 | 7.24 | 3.73 | 69.95 | 7.31 | 3.57 | free base HRMS, calc'd 339.1998, found 339.2001 |
| 23 | 103–108 | 67.14* | 8.90 | 4.12 | 67.16 | 8.49 | 4.31 | *.H$_2$O |
| 24 | 152–154 | 74.27 | 8.13 | 3.77 | 73.91 | 8.17 | 3.74 | |
| 25 | 170–172 | 73.38* | 8.17 | 3.72 | 73.28 | 8.13 | 3.72 | +.¼ H$_2$O |
| 26 | 154–156 | 76.54 | 7.41 | 3.43 | 76.36 | 7.41 | 3.43 | |
| 27 | gum | 70.29* | 8.04 | 3.73 | 70.73 | 7.95 | 3.46 | *.H$_2$O; free base HRMS, calc'd 321.2093, found 321.2099 |
| 28 | gum | 72.01* | 7.97 | 3.82 | 71.56 | 7.86 | 3.36 | *.0.5 H$_2$O; free base HRMS, calc'd 321.2093, found 321.2097 |
| 29 | | 65.15* | 8.14 | 3.17 | 65.21 | 8.16 | 3.81 | *.1.5 H$_2$O; free base MSCI = 299 (MH$^+$) |
| 30 | 105–107 | 71.46* | 8.19 | 3.47 | 71.45 | 8.23 | 3.90 | *.H$_2$O |
| 31 | 137–138 | 70.90 | 6.90 | 3.31 | 70.85 | 6.91 | 3.33 | |
| 32 | 98–99 | 70.40 | 6.65 | 3.42 | 70.47 | 6.52 | 3.41 | |
| 33 | 109–110 | 73.90 | 6.82 | 2.87 | 73.79 | 6.60 | 2.83 | |
| 34 | 140–142 | 84.59* | 7.86 | 3.72 | 84.14 | 7.76 | 3.30 | *on free base |
| 35 | 111–113 | 62.97* | 6.02 | 2.72 | 63.25 | 5.90 | 2.68 | *.0.5 H$_2$O |
| 36 | oil | 66.79* | 8.74 | 3.12 | 67.14 | 8.52 | 3.07 | *.H$_2$O; free base HRMS, calc'd 315.2562, found 315.2564 |
| 37 | gum | 70.90 | 6.90 | 3.31 | 71.13 | 6.84 | 3.10 | free base HRMS, calc'd 307.1936, found 307.1951 |
| 38 | gum | 70.90 | 6.90 | 3.31 | 70.96 | 6.76 | 3.20 | free base HRMS, calc'd 307.1936, found 307.1939 |

EXAMPLE 39

1-Phenethyl-4-(3-phenyl-2-propynyloxy)ethyl]piperidine, hydrochloride salt

Sodium hydride (0.912 g, 23 mmol, 60% oil disp.) which had been rinsed with hexanes (3×10 mL), and dry N,N-dimethylformamide (50 mL) were cooled to 0° C. with stirring under a nitrogen atmosphere. A solution of 1-t-butyloxycarbonyl-4-hydroxyethylpiperidine (4.3 g, 19 mmol) in dry DMF (15 mL) was added, and the mixture stirred for 1 hour. 3-Phenylpropargyl chloride (2.8 g, 19 mmol) was added, and the mixture was heated to reflux for 24 hours. After cooling, the solvent was removed by distillation under reduced pressure. The residue was u dissolved in ethyl acetate and extracted with water (3×100 mL), brine (100 mL), dried (MgSO$_4$), filtered, and concentrated under reduced pressure. The crude product was purified by chromatography on silica gel, eluting with 5% ethyl acetate in hexanes, and concentrated under reduced pressure to yield 1-t-butyloxycarbonyl-4-[(3-phenyl-2-propynyloxy)ethyl]piperidine (1.02 g, 16% dark oil. $^1$H NMR (300 MHz, CDCl$_3$/TMS, δ): 7.5(m,2H), 7.3(m,3H), 4.4(s,2H), 4.1(m,2H), 3.6(t,2H), 2.7(br t,2H), 1.8–1.1(m,16H). MSCI: 344 (MH$^+$, base).

The N-t-BOC. intermediate (500 mg, 1.46 mmol) was stirred with 3 M hydrogen chloride in ethyl acetate (10 mL) at room temperature for 2 hours, then concentrated in vacuo. The crude product was purified by chromatography on silica gel, eluting with 30% methanol in chloroform, then concentrated in vacuo to yield 4-[(3-phenyl-2-propynyloxy)ethyl]piperidine hydrochloride (340 mg, 83%). $^1$H NMR(300 MHz, CDCl$_3$/TMS, $\delta$): 7.42-7.30 (m,5H) 4.39(s,2H), 3.6(t,2H,J=6 Hz), 3.45(m,4H), 2.85(br t,2H), 1.9-1.6(m,8H). MSCI: 244(MH+, base).

The amine salt (0.34 g, 1.4 mmol), phenethyl bromide (0.26 g, 1.4 mmol), and potassium carbonate (0.50 g) were heated at reflux in absolute ethanol (50 mL) for 48 hours. After cooling, the mixture was filtered and concentrated in vacuo. The crude product was purified by chromatography on silica gel, eluting with 10% methanol in chloroform, and concentrated in vacuo to yield a colorless oil (0.25 g, 51%). $^1$H NMR(300 MHz, CDCl$_1$/TMS, $\delta$): 7.45-7.10(m,10H), 4.36(s,2H), 3.6(t,2H,J=6 Hz), 3.04-1.20(m,15H).

conversion to the hydrochloride salt was carried out as described earlier to yield a solid which melted at 130°-133° C. Analysis: Calculated for C$_{24}$H$_{29}$NO·HCl: C,75.20; H,7.83; N,3.66; found: C,75.50; H,7.77; N,3.51.

EXAMPLE 40

1-Benzyl-4-[(3-phenylpropynyloxy)methyl]piperidine

This compound was prepared for use Example 39 described above. Benzyl chloride was used for the amine alkylation to yield the free base as a solid which melted at 120°-123° C. HRMS: Calculated for C$_{23}$H$_{27}$NO: 333.2084; found: 333.2093.

EXAMPLE 41

(E)-1Benzyl-4-[(3-phenyl-2-propenyloxy)1ethyl]piperidine, maleic acid salt

Cinnamyl alcohol (1.52 g, 11.3 mmol) an sodium hydride (0.56 g, 14 mmol, 60% oil disp.) were stirred in dry N,N-dimethylformamide (15 mL) at room temperature under a nitrogen atmosphere for 45 minutes. After the hydrogen gas evolution had ceased, a solution of 1-benzoyl-4[(p-toluene sulfonyl)oxyethyl]piperidine (3.93 g, 11.3 mmol) in dry DMF (40 mL) was added, and the mixture was stirred for 18 hours. Additional sodium hydride (0.53 g) was added, and the reaction was further stirred for 24 hours. The reaction was quenched with saturated aqueous ammonium chloride (50 mL), and extracted with ethyl acetate (500 mL). The organic phase was extracted with water (5×50 mL), brine (50 mL), dried (MgSO$_4$), filtered, and concentrated in vacuo. The crude product was purified by chromatography on silica gel, eluting with hexanes to 50% ethyl acetate in hexanes, then concentrated under vacuum to yield (E)-1-benzoyl-4-[(3-phenyl-2-propenyloxy)ethyl]piperidine (2.55 g, 65%) as a yellow oil. IR (neat): 1630 cm$^{-1}$. HRMS: Calculated for C$_{23}$H$_{27}$NO$_2$: 349.2042; found: 349.2050.

Lithium aluminum hydride (1.0 M in tetrahydrofuran, 2.1 mL, 2.1 mmol) was added dropwise over 4 minutes to a −78° C. solution of the above amide (0.72 g, 2.1 mmol) in dry THF with stirring under nitrogen. After 3 hours, the reaction was allowed to slowly warm to room temperature. After 21 hours, Celite® was slurried into the reaction mixture, followed by careful quenching with water (20 mL). The mixture was filtered through a Celite® pad and rinsed with ethyl acetate (100 mL). After phase separation, the organic solution was extracted with water (20 mL), brine (20 mL), dried (MgSO$_4$), filtered, and concentrated in vacuo. The crude product was purified by chromatography on silica gel, eluting with ethyl acetate, and concentrated under vacuum to yield (E)-4-[(3-phenyl-2-propenyloxy)ethyl]piperidine (0.18 g, 26%) as a colorless oil. $^1$H NMR(300 MHz/CDCl$_3$/TMS, $\delta$): 7.40-7.16(m,10H), 6.60(d,1H,J=16 Hz), 6.29(dt,1H,J=16,6 Hz), 4.12(dd,2H,J=6,1 Hz), 3.51(t,2H,J=7 Hz), 3.48(s,2H), 2.88-2.85(m,2H), 2.00-1.21 (m,9H). HRMS: Calculated for C$_{23}$H$_{29}$NO:335.2249; found: 335.2251.

A solution of maleic acid (91 mg, 0.78 mmol) in tetrahydrofuran was added to a room temperature solution of the amine (0.26 g, 0.78 mmol) in chloroform (3 mL). The solution was concentrated in vacuo, and dried under high vacuum to yield the salt (0.35 g) as a waxy solid which melted at 77°-80° C. An analytical sample was dried under high vacuum at 56° C. overnight. Analysis: Calculated for hemihydrate C$_{23}$H$_{29}$NO·C$_4$H$_4$O$_4$·1/2 H$_2$O: C,70.41; H,7.44; N,3.04; found: C,70.68; H,7.68; N,2.89.

EXAMPLE 42

(Z)-1-Benzyl-4[(3-phenyl-2-propenyloxy)ethyl]piperidine

A solution of 1-t-butyloxycarbonyl-4-[(3-phenyl-2-propynyloxy)ethyl]piperidine (0.50 g, 1.5 mmol) in methanol (25 mL) containing 5% palladium on barium sulfate (25 mg) and freshly distilled synthetic quinoline (25 mg) was stirred at room temperature under 1 atmosphere of hydrogen until the calculated amount of hydrogen was taken up. The mixture was then filtered through a Celite® pad, rinsed, and concentrated in vacuo to yield (Z)-1-t-butyloxy-carbonyl-4-[(3-phenyl-2-propenyloxy)ethyl]piperidine contaminated by a minor amount of over-reduced material (0.50 g).

The crude product was N-deprotected and N-alkylated with benzylchloride under standard conditions. The crude product was purified by chromatography on silica gel, eluting with 20% methanol in chloroform, then concentrated to yield a solid (0.10 g) which melted at 68°-70° C. MSCI:336 (MH+, base).

Utility

The compounds of this invention and their pharmaceutically acceptable salts possess psychotropic properties, particularly antipsychotic activity of good duration with selective sigma receptor antagonist activities while lacking the typical movement disorder side-effects of standard dopamine receptor antagonist antipsychotic agents. These compounds can also be useful as antidotes for certain psychotomimetic agents such as phencyclidine (PCP), and as antidyskinetic agents.

In vitro

Sigma Receptor Binding Assay

Male Hartley guinea pigs (250-300 g, Charles River) were sacrificed by decapitation. Brain membranes were prepared by the method of Tam (Proc. Natl. Acad. Sci. USA 80: 6703-6707, 1983). Whole brains were homogenized (20 seconds) in 10 vol (wt/vol) of ice-cold 0.34 M sucrose with a Brinkmann Polytron (setting 8). The homogenate was centrifuged at 920 × g for 10 minutes. The supernatant was centrifuged at 47,000 × g for 20 minutes. The resulting membrane pellet was resuspended in 10 vol (original wt/vol) of 50 mM Tris HCl (pH 7.4) and incubated at 37° C. for 45 minutes to degrade and dissociate bound endogenous ligands. The membranes were then centrifuged at 47,000 × g for 20 minutes and resuspended in 50 mM Tris HCl (50 mL per brain).

0.5 mL aliquots of the membrane preparation were incubated with unlabeled drugs, 1 nM (+)-[$^3$H]SKF 10,047 in 50 mM Tris HCl, pH 7.4, in a final volume of 1 mL. Nonspecific binding was measured in the presence of 10 μM (+)-SKF 10,047. The apparent dissociation constant (Kd) for (+)-[$^3$H]SKF 10,047 is 50 nM. After 45 minutes of incubation at room temperature, samples were filtered rapidly through Whatman GF/C glass filters under negative pressure, and washed 3 times with ice-cold Tris buffer (5 mL).

IC$_{50}$s were calculated from log-logit plots. Apparent K$_i$s were calculated from the equation, $K_i = IC_{50}/[1+(L/K_d)]$ (4), where L is the concentration of radio ligand and K$_d$ is its dissociation constant. Data are shown in Table 4.

Dopamine Receptor Binding

Membranes were prepared from guinea pig striatum by the method described for sigma receptor binding. The membranes were then resuspended in 50 mM Tris HCl (9 mL per brain).

0.5 mL aliquots of the membrane preparation were incubated with unlabeled drugs, and 0.15 nM [$^3$H]spiperone in a final volume of 1 mL containing 50 mM Tris HCl, 120 mM NaCl and 1 mM MgCl$_2$ (pH 7.7). Nonspecific binding was measured in the presence of 100 nM (+)-butaclamol. After 15 minutes of incubation at 37° C., samples were filtered rapidly through Whatman GF/C glass filters under negative pressure, and washed three times with ice-cold binding buffer (5 mL).

IC$_{50}$s were calculated from log-logit plots. Apparent K$_i$s were calculated from the equation $K_i = IC_{50}[1+(L/K_d)]$ (4), where L is the concentration of radio ligand and K$_d$ is its dissociation constant. Data are shown in Table 4.

The data in Table 4 indicate that haloperidol, a typical antipsychotic drug, has potent binding affinity for both the sigma and dopamine receptors. This binding profile of haloperidol reflects the therapeutic activity as well as the motor side effects caused by antagonism of the dopamine receptors. In contrast, the examples of this invention shown in Table 4 indicate potent and selective binding affinity for sigma receptors without binding to the dopamine receptors. Therefore, these compounds are not expected to produce the extrapyramidal symptoms usually produced by haloperidol and other typical antipsychotics which are dopamine receptor antagonists.

TABLE 4

| EX. NO. | EXAMPLE | RECEPTOR BINDING SIGMA* | DOPAMINE D-2* |
|---|---|---|---|
|  | HALOPERIDOL | +++ | +++ |
| 21 | 21 | +++ | − |
| 22 | 22 | +++ | − |
| 23 | 23 | +++ | − |
| 24 | 24 | +++ | − |
| 25 | 25 | +++ | + |
| 26 | 26 | +++ | − |
| 27 | 27 | +++ | − |
| 28 | 28 | +++ | − |
| 29 | 29 | +++ | − |
| 30 | 30 | +++ | − |
| 31 | 31 | +++ | − |
| 32 | 32 | +++ | − |
| 33 | 33 | ++ | − |
| 34 | 34 | +++ | − |
| 35 | 35 | +++ | − |
| 36 | 36 | +++ | − |

TABLE 4-continued

| EX. NO. | EXAMPLE | RECEPTOR BINDING SIGMA* | DOPAMINE D-2* |
|---|---|---|---|
| 37 | 37 | +++ | − |
| 38 | 38 | +++ | − |
| 39 | 39 | +++ | + |
| 40 | 40 | +++ | − |
| 41 | 41 | +++ | − |
| 42 | 42 | ++ | − |

*Ki (nM): 1-30 (+++), 31-100 (++), 101-500 (+), >500 (−).

In Vivo

Isolation-Induced Aggression in Mice

This is a modification of the method of Yen et al. (Arch. Int. Pharmacodyn. 123: 179–185, 1959) and Jannsen et al. (J. Pharmacol. Exp. Ther. 129: 471–75, 1960). Male Balb/c mice (Charles River) were used. After 2 weeks of isolation in plastic cages (11.5×5.75×6 in) the mice were selected for aggression by placing a normal group-housed mouse in the cage with the isolate for a maximum of 3 minutes. Isolated mice failing to consistently attack an intruder were eliminated from the colony.

Drug testing was carried out by treating the isolated mice with test drugs or standards. Fifteen minutes after dosing with test drugs by the oral route, one isolated mouse was removed from its home cage and placed in the home cage of another isolate. Scoring was a yes or no response for each pair. A maximum of 3 minutes was allowed for an attack and the pair was separated immediately upon an attack. Selection of home cage and intruder mice was randomized for each test. Mice were treated and tested twice a week with at least a 2 day washout period between treatments.

As shown in Table 5, haloperidol and Examples 21 and 25 all were effective in inhibiting the isolation-induced aggressive behavior indicating psychotropic activities.

TABLE 5

| Example | In Vivo Inhibition of Isolation-induced Aggression* |
|---|---|
| Haloperidol | +++ |
| 21 | + |
| 25 | + |

*ED$_{50}$ (mg/kg): ≦10 (+++), 11-20 (++), 21-70 (+), >70 (−).

Dosage Forms

Daily dosage ranges from 1 mg to 2000 mg. Dosage forms (compositions) suitable for administration ordinarily will contain 0.5–95% by weight of the active ingredient based on the total weight of the composition.

The active ingredient can be administered orally in solid dosage forms, such as capsules, tablets, and powders, or in liquid dosage forms, such as elixirs, syrups, and suspensions; it can also be administered parenterally in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, A. Osol, a standard reference text in this field.

What is claimed is:

1. A method of inhibiting psychoses in a mammal which comprises administering to the mammal an effective amount of a compound of formula:

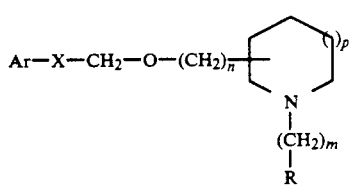

(I)

wherein:
n is 0, 1, or 2;
p is 0 or 1;
m i 1,2, or 3;
X is —C≡C— or $R^1C=CR^2$ (cis or trans);
$R^1$ and $R^2$ independently are H, alkyl of 1–4 carbon atoms, or phenyl;
Ar is naphthyl or phenyl, optionally substituted with 1–5 substituents individually selected form $NO_2$, halogen, $CF_3$, SH, alkyl of 1–4 carbon atoms, alkoxy of 1–4 carbon atoms, hydroxy alkyl of 1–4 carbon atoms, —C(=O)—$R^3$, —$NR^3R^4$, —C(=O)—$NR^3R^4$, —$NR^3C(=O)R^4$ S(O)q$R^5$ where q is 0, 1, or 2;
$R^3$ and $R^4$ independently are H, alkyl of 1–4 carbon atoms, or phenyl;
$R^5$ is alkyl of 1–4 carbon atoms or phenyl;
R is H, alkyl of 1–5 carbon atoms, cycloalkyl of 3–6 carbon atoms, Arl where Arl is phenyl or naphthyl, or —CH=$CR^6R^7$; and
$R^6$ and $R^7$ independently are H or alkyl of 1–4 carbon atoms, provided that when n=0 the side chain is not located at the 2-position of the ring; or po1 a pharmaceutically acceptable salt thereof.

2. A method of inhibiting psychoses in a mammal which comprises administering to the mammal an effective amount of a compound of formula I in claim 25 where n and p are 1.

3. .A method of inhibiting psychoses in a mammal which comprises administering to the mammal an effective amount of a compound of formula I in claim 25 where m is 1.

4. A method of inhibiting psychoses in a mammal which comprises administering to the mammal an effective amount of a compound of formula I in claim 25 wherein R is phenyl.

5. A method of inhibiting psychoses in a mammal which comprises administering to the mammal an effective amount of a compound of formula I in claim 25 wherein X is trans —CH=CH—.

6. A method of inhibiting psychoses in a mammal which comprises administering to the mammal an effective amount of a compound of formula I in claim 1 wherein Ar is phenyl, p-F-phenyl or p-$CR_3$-phenyl.

7. A method of inhibiting psychoses in a mammal which comprises administering to the mammal an effective amount of a compound of formula I in claim 1 wherein the side chain is attached to the 4-position of the piperidine ring.

8. A method of inhibiting psychoses in a mammal which comprises administering to the mammal an effective amount of a compound of claim 1, (E)-1-benzyl-4-[(3-phenyl-2-propenyloxy)methyl]-piperidine.

9. A method of inhibiting psychoses in a mammal which comprises administering to the mammal an effective amount of a compound of claim 1, (E)-1-benzyl-4-{[3-(4-fluoro)phenyl-2-propenyloxy]methyl}-piperidine.

10. A method of inhibiting psychoses in a mammal which comprises administering to the mammal an effective (E)-1-phenethyl-4-[(3-phenyl-2-propenyloxy)methyl]-piperidine.

11. A method of inhibiting psychoses in a mammal which comprises administering to the mammal an effective (E)-1-(3-phenyl)propyl-4-[(3-phenyl-2-propenyloxy)methyl]-piperidine.

12. The method of claim 1 wherein:
n and p are 1;
m is 1–3;
R is phenyl;
X is trans —CH=CH—;
Ar is phenyl, p+F-phenyl or p-$CF_3$-phenyl; and
wherein the side chain is attached to the 4-position of the piperidine ring.

13. The method of claim 1 wherein the compound is selected from the group:
(E)-1-benzyl-4-[(3-phenyl-2 propenyloxy)methyl] piperidine;
(E)-1-benzyl-4-[{3-(4-fluoro)phenyl-2-propenyloxy]methyl} piperidine;
(E)-1-phenethyl-4-[(3-phenyl-2-propenyloxy)methyl] piperidine;
(E)-1-(3-phenyl)propyl-4-[(3-phenyl-2-propenyloxy)-methyl]-piperidine; and
(E)-1-benzyl-4-{[3-(4-trifluoromethyl)phenyl-2-propenyloxy]methyl}-piperidine.

* * * * *